(12) United States Patent
Okimoto et al.

(10) Patent No.: US 7,454,293 B2
(45) Date of Patent: Nov. 18, 2008

(54) METHODS FOR ENHANCED DETECTION AND ANALYSIS OF DIFFERENTIALLY EXPRESSED GENES USING GENE CHIP MICROARRAYS

(75) Inventors: Gordon S. Okimoto, Honolulu, HI (US); Charles Boyd, Honolulu, HI (US); Johann Urschitz, Honolulu, HI (US)

(73) Assignee: University of Hawai'i, Honolulu, HI (US)

( * ) Notice: Subject to any disclaimer, the term of this patent is extended or adjusted under 35 U.S.C. 154(b) by 566 days.

(21) Appl. No.: 11/031,463

(22) Filed: Jan. 7, 2005

(65) Prior Publication Data

US 2005/0181399 A1 Aug. 18, 2005

Related U.S. Application Data

(60) Provisional application No. 60/535,433, filed on Jan. 7, 2004.

(51) Int. Cl.
*G06F 19/00* (2006.01)
*C12Q 1/68* (2006.01)

(52) U.S. Cl. .............................. 702/19; 435/6
(58) Field of Classification Search ........................ None
See application file for complete search history.

(56) References Cited

U.S. PATENT DOCUMENTS 6,351,712 B1 * 2/2002 Stoughton et al. ............. 702/19
2002/0019704 A1 2/2002 Tusher

FOREIGN PATENT DOCUMENTS

WO WO 02/057426 7/2002

OTHER PUBLICATIONS

Morgan et al. Frequent sampling reveals Dynamic responses by the Transcriptome to Routine Media replacement in HepG2 Cells. Toxicologic Pathology vol. 31, pp. 448-461 (2003).*
Klevecz et al, "Genome Wide Oscillations in Expression", Mol.Biol. Rpts. 2001, vol. 28, p. 73-82.
Morgan et al, "Frequent Sampling Reveals Dynamic Responses by the Transcriptome . . . ", Toxicologic Path. 2003, vol. 31, p. 448-461.

* cited by examiner

*Primary Examiner*—John S Brusca
(74) *Attorney, Agent, or Firm*—Leighton K. Chong

(57) ABSTRACT

A method for enhanced detection and statistical analysis of differentially expressed genes in gene chip microarrays employs: (a) transformation of gene expression data into an expression data matrix (image data paradigm); (b) wavelet denoising of expression data matrix values to enhance their signal-to-noise ratio; and (c) singular value decomposition (SVD) of the wavelet-denoised expression data matrix to concentrate most of the gene expression signal in primary matrix eigenarrays to enhance the separation of true gene expression values from background noise. The transformation of gene chip data into an image data paradigm facilitates the use of powerful image data processing techniques, including a generalized logarithm (g-log) function to stabilize variance over intensity, and the WSVD combination of wavelet packet transform and denoising and SVD to clearly enhance separation of the truly changed genes from background noise. Detection performance can be assessed using a true false discovery rate (tFDR) computed for simulated gene expression data, and comparing it to estimated FDR (eFDR) rates based on permutations of the available data. Where a small number (N) of samples in a group is involved, a pair of specific WSVD algorithms are employed complementarily if N>5 and if N<6.

19 Claims, 9 Drawing Sheets

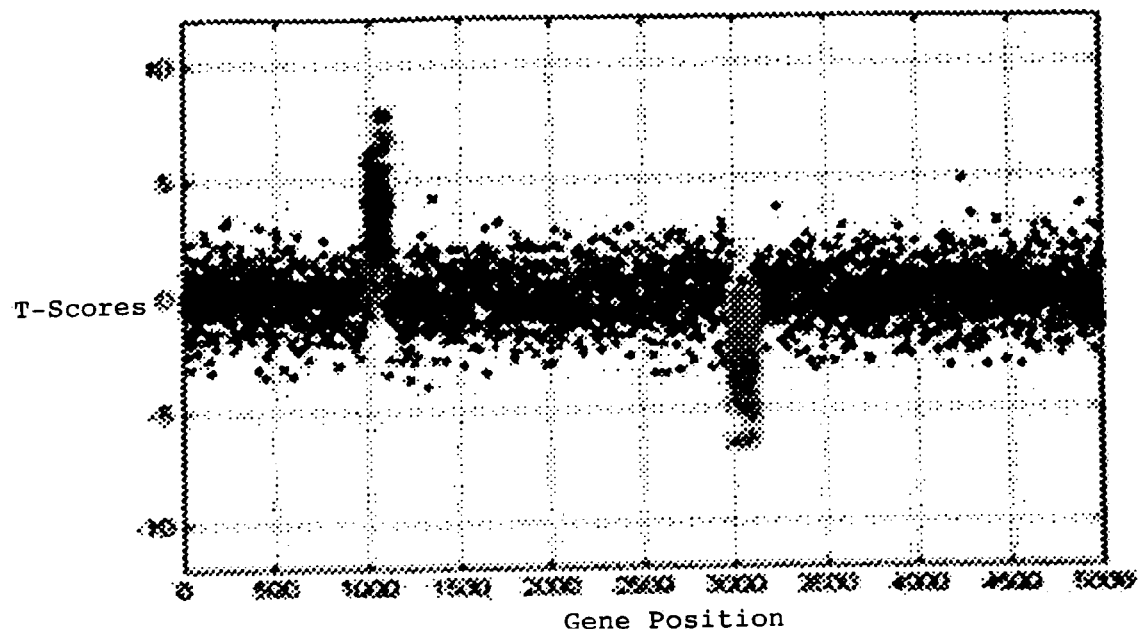
Figure 3B T-scores before WSVD processing
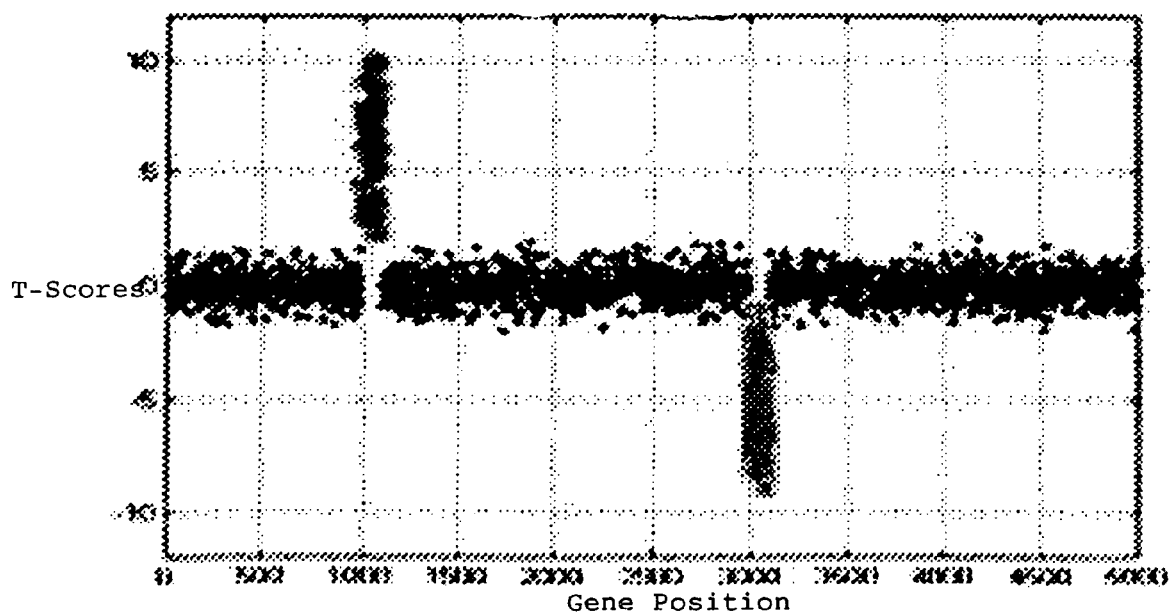
Figure 4 T-scores after WSVD processing

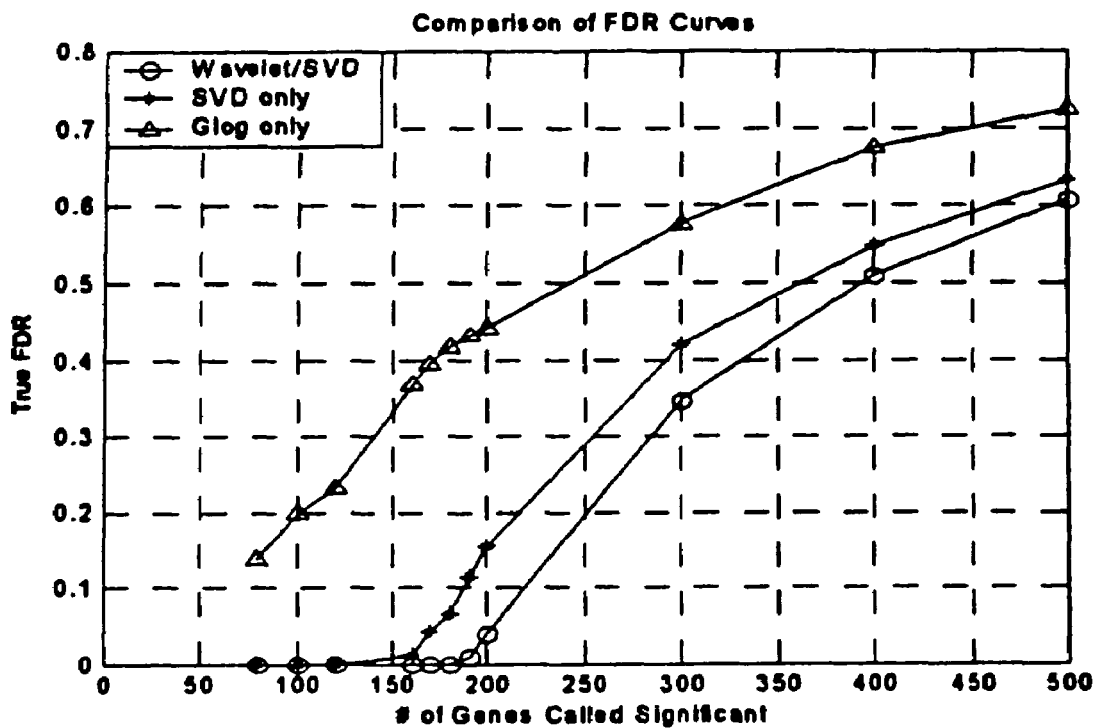
Figure 5. Comparison of tFDR curves
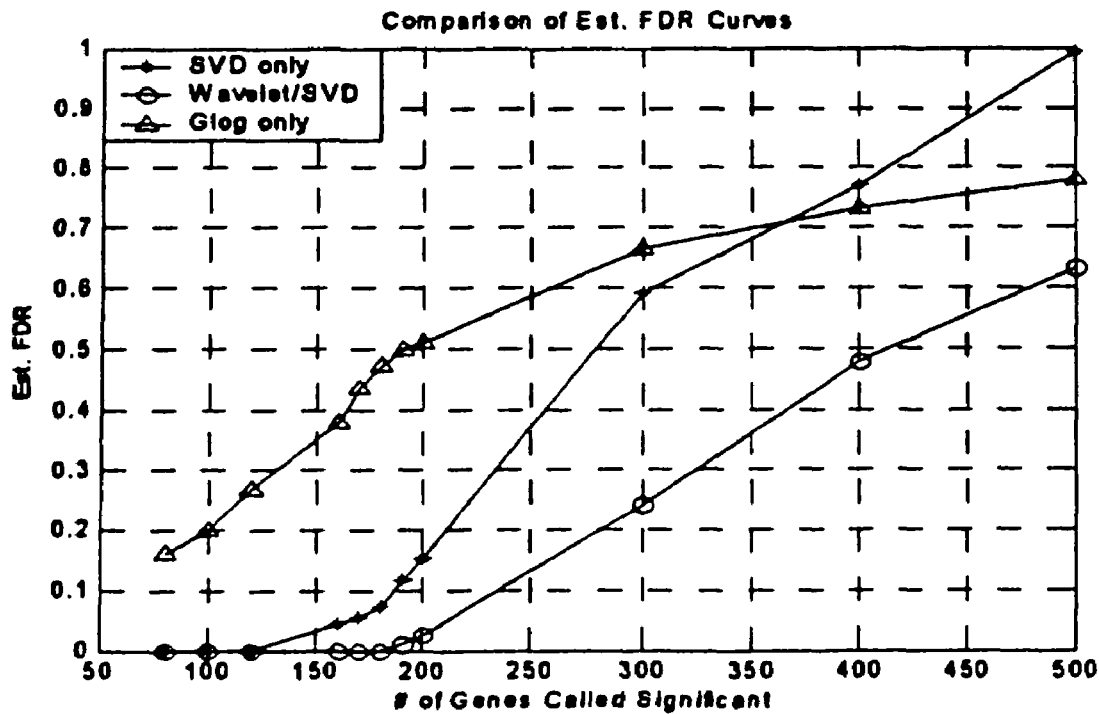
Figure 6. Comparison of eFDR curves

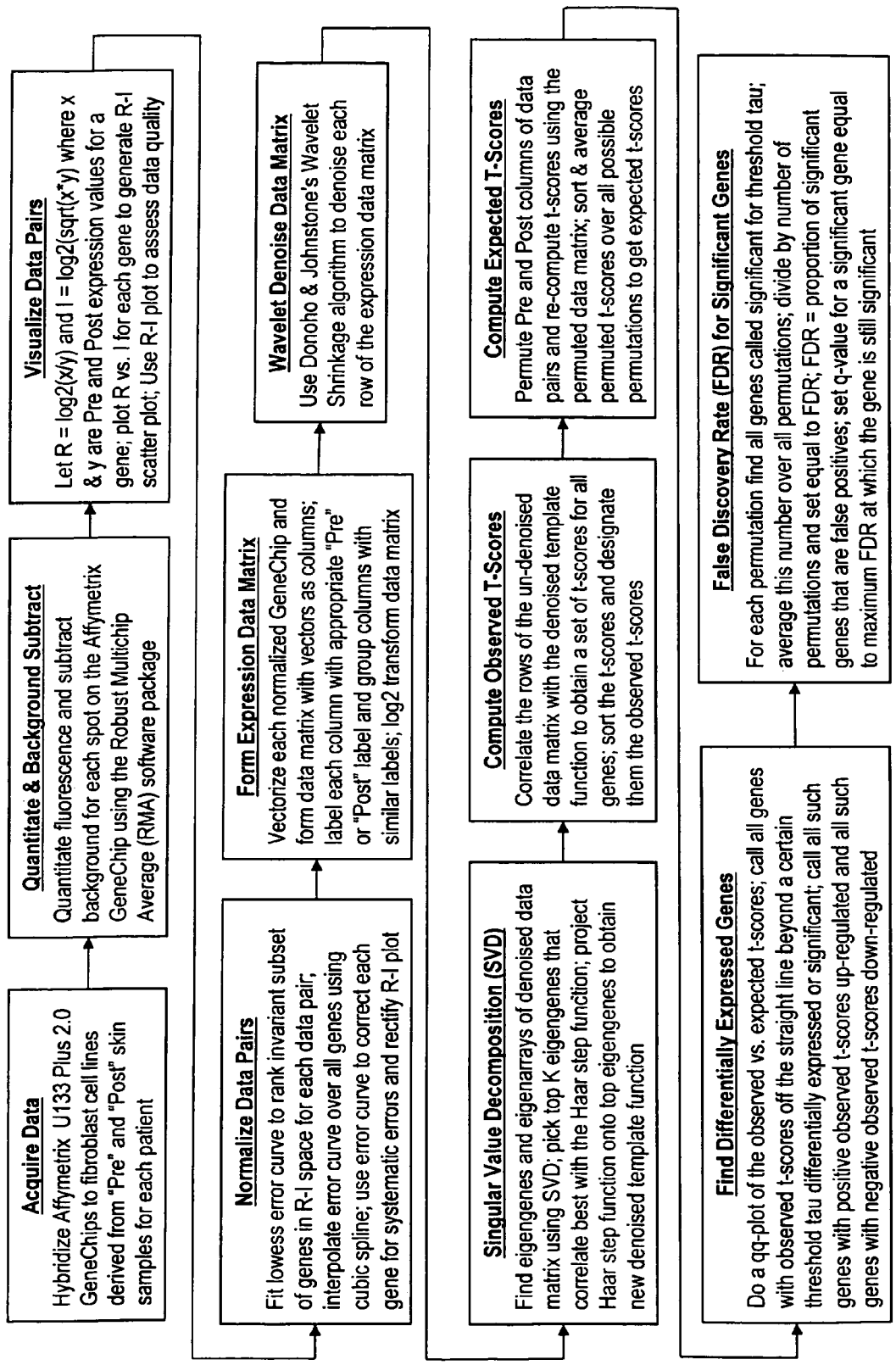
FIGURE 7 (Flow Chart for N>5 WSVD Algorithm)

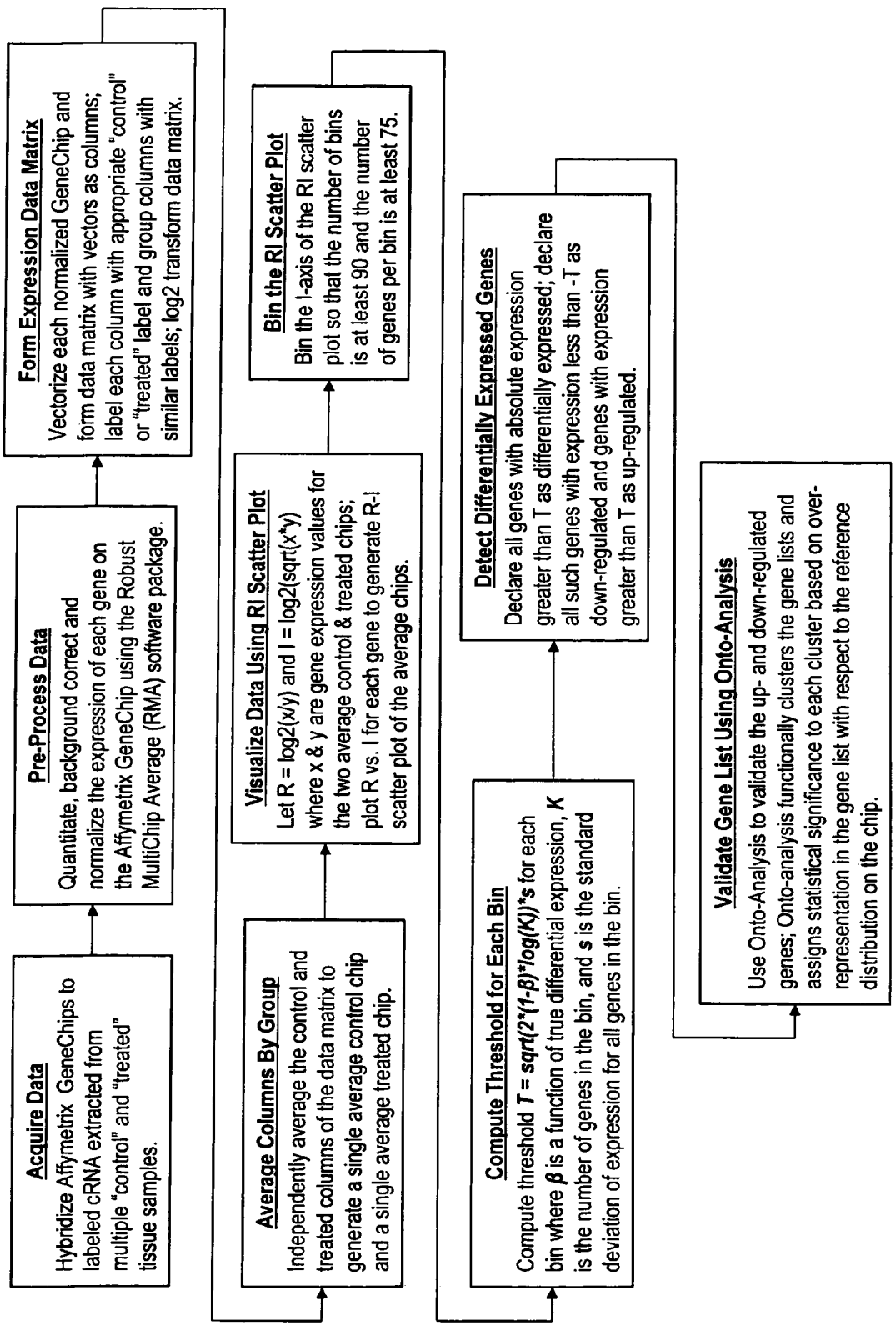
FIGURE 8 (Flow Chart for N<6 (WaveThresh) Algorithm)

METHODS FOR ENHANCED DETECTION AND ANALYSIS OF DIFFERENTIALLY EXPRESSED GENES USING GENE CHIP MICROARRAYS

This U.S. patent application claims the priority of U.S. Provisional Application No. 60/535,433 filed on Jan. 7, 2004, entitled "Data Transformation Method for Enhanced Detection of Differentially Expressed Genes With Gene Chip Microarrays", of the same inventors.

TECHNICAL FIELD

This invention relates in general to detection and statistical analysis of gene expression data and, in particular, to statistical analysis of microarray data for identifying genes that are differentially expressed in biological samples for medical research.

BACKGROUND OF INVENTION

Living things have unique genomes that are characterized by differences in the copy number of genes or in levels of transcription of protein agents from genes within their cellular environments. By detection and analysis of such genomic data, insight can be gained into the unique genetic makeup of such living things. In particular, the detection and analysis of differential gene expression in human subjects as indicators of the causes of or propensities toward certain diseases can lead to the discovery of genetic markers for those diseases and the development of pharmaceuticals and treatments to cure such diseases.

Although in principle the human genome contains all the information one would need to determine the genetic makeup of a person and the causes or disposition of that person to certain diseases, in actuality the genetic information is encoded in complex ways and is subject to complex stages of transcription and change into final protein agents, which are themselves subject to intermediation by multiple physical and biological constructs that have yet to be fully understood. It is generally understood that the human genome consists of some 22,000 to 24,000 genes, which, through complex transcription sequences and interactions can result in a currently estimated 2,000,000 different protein agents in the body. The combined effect of genome-level variations and physical and biological interactions makes it difficult to predict the expression of any particular gene or gene grouping, and even more difficult to predict the result of a final transcription of a protein agent and its effect in the body. The genome-centric view of molecular biology of the recent past is thus evolving into a more comprehensive "systems" view in which comprehensive information at the various transcriptional levels from genes to proteins to effects in the body are gathered in dispersed databases and harnessed together in a pipeline from research to discovery. The ideal vision for developing and harnessing such comprehensive knowledge is ultimately "personalized medicine", in which a complete description of a person's clinical symptoms, medical history, gene-expression data, metabolic parameters, and treatment results can lead to finding the causes and the cures for any diseases experienced by that person. For a more complete overview of this subject, reference is made to Augen, J., "Bioinformatics in the Post-Genomic Era", Addison Wesley, 2004.

The development of a complete molecular-level picture of health and disease involves understanding metabolic processes at four distinct levels: genome (DNA sequence), transcriptome (messenger RNA profile), proteome (protein structure and interactions), and metabolic pathway (action and effect in the body). Messenger RNA (or mRNA) profiling technologies are emerging as standard tools for research and clinical use in all these levels. It has become apparent that the transcription expression of large numbers of genes (if not the entire genome) needs to be determined in parallel to achieve an understanding of complex metabolic events. For example, it is estimated that as many as 10% of the 10,000 to 20,000 mRNA species in a typical mammalian cell are differently expressed between cancerous and normal tissues.

In simplistic terms, a gene impacts biological function by transcribing its DNA sequence into messenger RNA (mRNA), which in turn is translated into a corresponding protein. Proteins are the molecular components that directly control all biological systems. A gene is "expressed" if it is actively transcribing mRNA. The DNA hybridization array (also referred to as microarrays, expression arrays, or gene chips) has become the dominant technology for quantifying the expression of many genes in parallel because of its low cost and flexibility. DNA microarrays allow a biologist to obtain a snap-shot of the expression levels of a large set or all of the genes of a subject genome in a given tissue sample at a given point in time. Using DNA chips, patterns of global gene expression can be compared between normal and abnormal tissue samples to detect genes that are significantly changed in the abnormal condition. Gene expression data analysis can also be used to determine how genes change their expression in a single tissue sample over time. Detecting the set of all "differentially expressed" genes over space and time is an essential first step toward a comprehensive understanding of the pathobiology of many common diseases. Such understanding can lead to new diagnostic and prognostic applications and novel therapeutic interventions and drugs.

A DNA microarray is constructed with thousands of gene sequence fragments encoded as spots or points on a substrate, including known or predicted variants and potential polymorphisms to support a large number of cross comparisons of expression data. mRNA is harvested from selected cells in treated or symptomatic subjects as well as from control or untreated subjects, and reverse transcribed into more stable, complementary DNA (cDNA) added with fluorescent labels, green for cDNA derived from treated cells, and red for cDNA from untreated cells. The samples of fluorescent labeled cDNA are applied to the microarray and exposed to every spot. A sequence match results in binding between the cDNA test sequence and a complementary DNA sequence on the array (hybridization) resulting in fluorescent labeling of the spot. A laser fluorescent scanner is used to detect the hybridization signals from both fluorophores, and the resulting pattern of colored spots is stored in a database: green for strongly expressed genes in the treated sample, red for strongly expressed genes in the untreated sample, and black for sequences that are not expressed in either sample. Because the sequence of every spot in the chip is known, the identity of each expressed cDNA sequence can be determined, and the relative amount and source (treated or untreated sample) can be inferred from the color and intensity of the spot.

Microarrays with probes of various types can be employed for testing different expression patterns in a study's subjects. One type of microarray is the oligonucleotide microarray, such as the Gene Chip™ microarray offered by Affymetrix Corporation, of Palo Alto, Calif. For measuring gene expression levels using oligonucleotide microarrays, expected RNA transcripts of target genes can be measured by probes which are perfectly complementary to the target sequences (referred to as perfect match PM probes). Probes may also be provided whose sequences are deliberately selected not to match the target sequences (referred to as mismatched MM control probes). Since sequences that are different from the target sequences may also bind to the PM probes that correspond to particular target sequences, the fluorescence signals from such sequences would appear as noise. Signal-to-noise ratio can be improved by calculating the difference between signals from sequences that bind to PM probes and signals from sequences that bind to MM probes.

Due to the large amounts of data generated for entire genomic sets, for example, about 22,000 to 24,000 genes in the case of human beings, advanced quantitative methods are needed to determine whether detected differences in gene expression in microarray probes are experimentally significant. To point the way toward possible discovery and treatment of diseases indicated in small groups of human subjects, perhaps even an individual test subject, it would be desirable to have a method which can analyze a relatively small number of samples and provide a measure of acceptable statistical confidence in the detection of a particular gene expression pattern in the small test group.

Prior methods of small-group detection have been based on conventional t-tests to provide a probabilistic assessment that a detected gene expression pattern is significant, as opposed to a false positive detected randomly in noise. In conventional t tests, a false positive probability of 1% (p=0.01) may be deemed significant in experiments involving a small number of genes, however, in a microarray experiment for 10,000 genes, a 1% false positive probability would identify 100 genes expressed by chance as significant. Moreover, the amount and type of unwanted variations in DNA chip data makes discriminating true differential expression from noise a difficult task. Finally, the small number of DNA chip samples in any given study relative to the large number of genes renders classical statistical methods ineffective and error-prone.

One approach for further differentiating statistical significance of microarray data from false positives is known as the "fold change" method. In this method, a number of genetic samples are deliberately subjected to a physical change, such as a chemical reaction or physical manipulation or exposure (e.g., radiation), and their gene expression is compared to other samples that have not been subjected to such physical change. The "fold change" method is used to identify gene expression differences deemed significant in the samples subjected to the physical change compared to the samples not subjected to the physical change above a determined threshold. However, the "fold change" method is limited by the types of physical changes that can be employed corresponding to particular diseases or risk propensities being tested, and can also yield unacceptably high false discovery rates. Some attempts to improve on the "fold change" method, such as observing a fold change consistently between paired samples, is still limited and can yield an unacceptably high false discovery rate. See, Quackenbush J., Microarray data normalization and transformation, (2002) Nature Genetics Supplement, Vol. 32, 496-501.

As also noted above, conventional techniques analyze differences in gene expression levels that are both positive (up-regulated) and negative (down-regulated), so that negative expression values are possible during analysis. A standard method of "visualizing" both up-regulated and down-regulated genes between two (2) biological conditions plots fold change against the geometric average of expression in log-log scale. The resulting Ratio-Intensity (RI) plot displays differentially expressed genes on the periphery of the data cloud. Moreover, a typical RI scatter plot shows that variation of fold change is dependent on intensity, a situation which complicates statistical analysis and interpretation of results.

Another method of statistical analysis of gene expression data is the so-called "Significance Analysis of Microarrays" (SAM), for example, as disclosed in U.S. patent application 2002/019,704 of Tusher, V., Tibshirani, R., and Chu, C., published on Feb. 14, 2002. This method identifies genes with statistically significant differences in expression by assigning each gene a modified t-score representing differences in gene expression relative to a standard deviation of repeated measurements for that gene. Genes with absolute scores greater than an adjustable threshold are deemed potentially significant. A smoothing factor incorporated into the modified t-score renders the resulting analysis substantially independent of the ranges of values that characterize the genes. A confidence measure known as the false discovery rate (FDR) is used to assess the statistical significance of the collection of genes called significant by SAM. FDR is defined as the expected proportion of false positives among all genes called significant. The goal is to obtain a reasonably large list of significant genes with acceptably small FDR. A major feature of FDR as implemented in SAM is the automatic accounting for bias introduced by multiple testing of thousands of genes at once (i.e., multiple testing problem). Unlike the standard Bonferroni adjustment for multiple testing, FDR maintains sensitivity for differential expression without sacrificing specificity. FDR also allows genomic researchers to assess the risk of allocating more time and resources to a specific gene or group of genes. Finally, SAM uses permutation testing to estimate FDR for a given set of significant genes, thus precluding the need for distributional assumptions about the data under the null hypothesis of no differential expression. As a result, SAM analysis of microarray experiments involving small numbers of DNA chips are problematic since the number of permutations will be insufficient to accurately estimate the true FDR.

SUMMARY OF INVENTION

It is therefore a principal object of the present invention to provide a statistical analysis methodology that can analyze any number of microarray samples having thousands of gene probes per sample and, in particular, can detect specific differential gene expression patterns in a relatively small test group with an acceptable statistical confidence level. It is a particular object of the invention to provide a data pre-processing algorithm that improves the signal-to-noise ratio (SNR) of the expression data set such that the detection of differentially expressed genes is significantly enhanced as measured by standard metrics of performance such as Receiver Operating Characteristic (ROC) curves and FDR curves. SNR as a measure of signal quality broadens the focus of the standard statistical analysis from a noise-only characterization of differential expression to one that characterizes both signal and noise. This comprehensive approach to the modeling of differential gene expression leads to algorithms that are better able to detect genes with weak differential expression (DE) due to small sample size and low SNR.

In accordance with the present invention, a method for enhanced detection and analysis of microarray samples each containing a large set of microarray gene probes comprises the steps of:

(a) transforming the microarray samples data into an M×N expression data matrix of M rows of microarray gene probes and N columns of microarray gene expression values for the subject samples;

(b) using a 2-dimensional wavelet transform to transform the expression data matrix into wavelet domain with denoising to enhance signal-to-noise ratio (SNR) of the expression data matrix; and (c) applying a singular value decomposition (SVD) method to the wavelet-transformed and denoised expression data matrix in order to extract principal signals representing statistically significant differential gene expression patterns from the microarray data.

Transforming the microarray data into an M×N expression data matrix essentially converts the data into the paradigm of 2-D image data. Wavelet denoising is especially well suited for the subsequent microarray data analysis since it can reduce background noise without degrading the transient signal features characteristic of differential gene expression. In the preferred embodiment, the raw microarray data are also subjected to a generalized logarithm (glog) transformation to stabilize variance over intensity of expression values. The glogged expression data matrix is transformed into the wavelet domain using a 2-D wavelet packet transform. The wavelet packet transform generalizes the standard wavelet transform by decomposing both the approximation and detail signal simultaneously. In the wavelet domain, coherent signal components are localized at the larger scales of resolution while noise is confined to the smaller scales. This separation of signal from noise allows the use of simple yet powerful denoising techniques based on the thresholding of wavelet coefficients. Coefficients with small absolute value are either set to zero or reduced and then what remains is inverted using the inverse wavelet packet transform to obtain a denoised version of the original matrix. This denoised matrix has a more uniform noise background, and enhanced signal and higher SNR. This higher SNR translates to enhanced sensitivity and specificity in detecting genes that are differentially expressed under different biological conditions when further processed using a technique known as singular value decomposition (SVD).

SVD is a statistical technique for characterizing the linear correlation that exists in a set of data. SVD is used to decorrelate the whole-genome expression values into orthogonal components known as eigenarrays. That is, let A be an M×N expression data matrix that has been normalized, glogged and row-centered. Wavelet denoising is applied to the matrix A to obtain denoised matrix A' with enhanced SNR. The principal eigenarrays of A' are then extracted using SVD. The SVD of A is given by $A=U*S*V^T$ where the columns of U are the eigenarrays, the columns of V are the eigengenes and the square of the diagonal elements of S are the eigenvalues of A. The eigenarrays are arranged so that first eigenarray has the largest eigenvalue, the second eigenarray has the next largest eigenvalue and so on. The eigenvalue for an eigenarray measures the amount of variation in the data captured by that eigenarray. Usually, the first k eigenarrays capture most of the coherent signal in the data. These eigenarrays are called the principal eigenarrays.

To enhance detection of differential gene expression, standard t-scores are computed based on the matrix A. Enhanced t-scores are obtained by performing a least squares fit of the standard t-scores onto the principal eigenvectors. SVD assigns to each gene an enhanced t-score based on the most significant eigenarrays of the SVD decomposition. Moreover, the associated eigengene provides information on which samples are contributing the most to the differential expression signal captured by the most significant eigenarray. With this novel gene data transformation method, researchers can isolate both differential expression and the subset of DNA chips responsible for the observed effect. The "bad" samples can then be excluded from subsequent analysis to improve detection performance.

Permutation testing based on the enhanced t-scores is used to assign an estimated false discovery rate (eFDR) to a user-defined subset of genes deemed significantly changed based on SVD-enhanced t-scores. FDR is a statistical percentage of genes of a given set of significantly changed genes that are expected to be false positives, i.e., not really changed at all. Tests conducted on simulated gene expression data resulted in a true measured FDR rate that proved to be close to the estimated FDR rate calculated in the invention method.

The invention method further encompasses a complementary pair of algorithmic approaches depending on whether only a small number of samples in a group are available for analysis:

(A) If the number of samples in a group is greater than 5, then it proceeds with the following steps:
  (1) Vectorize appropriately normalized microarray data to form an M×N expression data matrix of M genes (rows) and N microarrays (columns) where the columns are grouped by biological condition (supervising vector);
  (2) Apply a wavelet shrinkage technique based on a 1-dimensional wavelet packet transform to denoise each row of the expression data matrix to improve signal-to-noise ratio (SNR);
  (3) Apply singular value decomposition (SVD) to the denoised data matrix to extract eigenarrays and eigengenes;
  (4) Correlate eigengenes with a Haar step function (which takes on the value of +1 on treatment chip-samples and −1 on control chip-samples) and sort the resulting values in descending order;
  (5) Pick the top K (K>0) eigengenes that correlate best with the Haar step function (principal eigengenes);
  (6) Perform a least squares fit of the Haar step function on the principal eigengenes to obtain an empirical supervising vector to be used for correlation detection of differentially expressed genes;
  (7) Correlate each un-denoised expression data for a gene with the denoised supervising vector described in step (6) to obtain a WSVD score for differential expression for each gene;
  (8) Apply a threshold to the WSVD score for each gene to determine a set of s differentially expressed genes;
  (9) Estimate the false discovery rate (FDR) for the determined set of differentially expressed genes; and
  (10) Modify the threshold for WSVD scores and repeat steps (8) and (9) until a significant set of differentially expressed genes with acceptable FDR is obtained; otherwise (B) If the number of samples in a group is less than 6, then it proceeds with the following steps:
  (1) Vectorize appropriately normalized microarray data to form an M×N expression data matrix of M rows (genes) and N columns (microarrays) where the columns are grouped as "treated" and "control" response classes in accordance with chip labels;
  (2) Compute a single column vector, X, equal to the geometric mean of all sample chips in the treated response class;
  (3) Compute a single column vector, Y, equal to the geometric mean of all sample chips in the control response class;
  (4) Form an RI scatter plot having an R axis and an I axis where $I=\log2(X \times Y)$ and $R=\log2(X/Y)$;

(5) Adaptively apply a binning technique to the I-axis of the RI scatter plot to ensure that each bin contains at least K genes per bin where K>75;
(6) Estimate the median absolute deviation (MAD) of expression values within each bin;
(7) Apply a threshold to each bin above and below zero using the value T=sqrt[2×(1−β)×log(K)]×MAD where:
   (a) $\beta = \log(\pi_0)/\log(\pi_1)$
   (b) log=natural logarithm
   (c) $\pi_0$=number of genes differentially expressed
   (d) $\pi_1$=total number of genes; and
(8) Declare genes within a bin having a score greater than T as differentially expressed, as follows:
   (a) Call genes with score >T as differentially up-regulated
   (b) Call genes with score <−T as differentially down-regulated.

Other objects, features, and advantages of the present invention will be explained in the following detailed description having reference to the appended drawings.

BRIEF DESCRIPTION OF DRAWINGS

FIG. 3B shows a scatter plot of t-scores of gene expression data prior to WSVD processing of the gene expression data.

FIG. 4 shows a scatter plot of t-scores after WSVD processing, illustrating a marked separation of changed genes from thinned-out background noise.

FIG. 5 shows a true false detection rate (tFDR) computed from simulated data for gene significance points ranging from 80 genes to 500 genes, comparing the WSVD, SVD-only, and GLOG-only processing of gene expression data.

FIG. 6 shows an estimated FDR rate (eFDR) computed for the gene significance points, showing that the results of WSVD processing are uniformly better than SVD-only or GLOG-only processing.

FIG. 7 is a flowchart of the steps in the specific algorithmic approach to WSVD processing when only a small number of samples N>5 are available in a group.

FIG. 8 is a flowchart of the steps in the specific algorithmic approach to WSVD processing when only a small number of samples N<6 are available in a group.

DETAILED DESCRIPTION OF INVENTION

The present invention is directed to a novel method for enhanced detection and statistical analysis of gene expression data, which can identify high-confidence gene expression patterns in subject samples that would be suitable for studies in biomarker discovery, drug target validation, molecular diagnosis and prognosis, drug toxicity prediction, and a systems-level understanding of disease biology. Detecting differentially expressed genes is essentially a computationally intensive pattern recognition problem. A person familiar with this field will appreciate that the data generated by sophisticated statistical analysis methods of comparing gene expression data from microarray chip samples having thousands of gene probes thereon can be extremely complex and computationally intensive involving powerful parallel processing platforms. Sophisticated bioinformatics programming and data handling techniques are required. As such techniques would be well understood to those skilled in this field, they are only referenced but not described in detail herein, and other references are provided so that the reader can refer to them for a more in-depth explanation thereof.

Figure 1A:
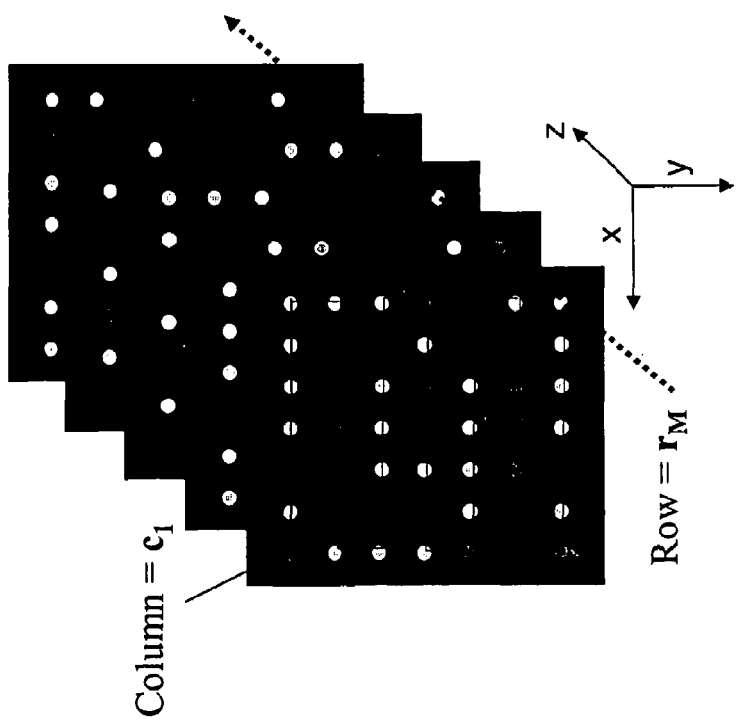
FIG. 1A illustrates conversion of gene expression data into an expression data matrix (image data paradigm) in accordance with the present invention.
Figure 1B:
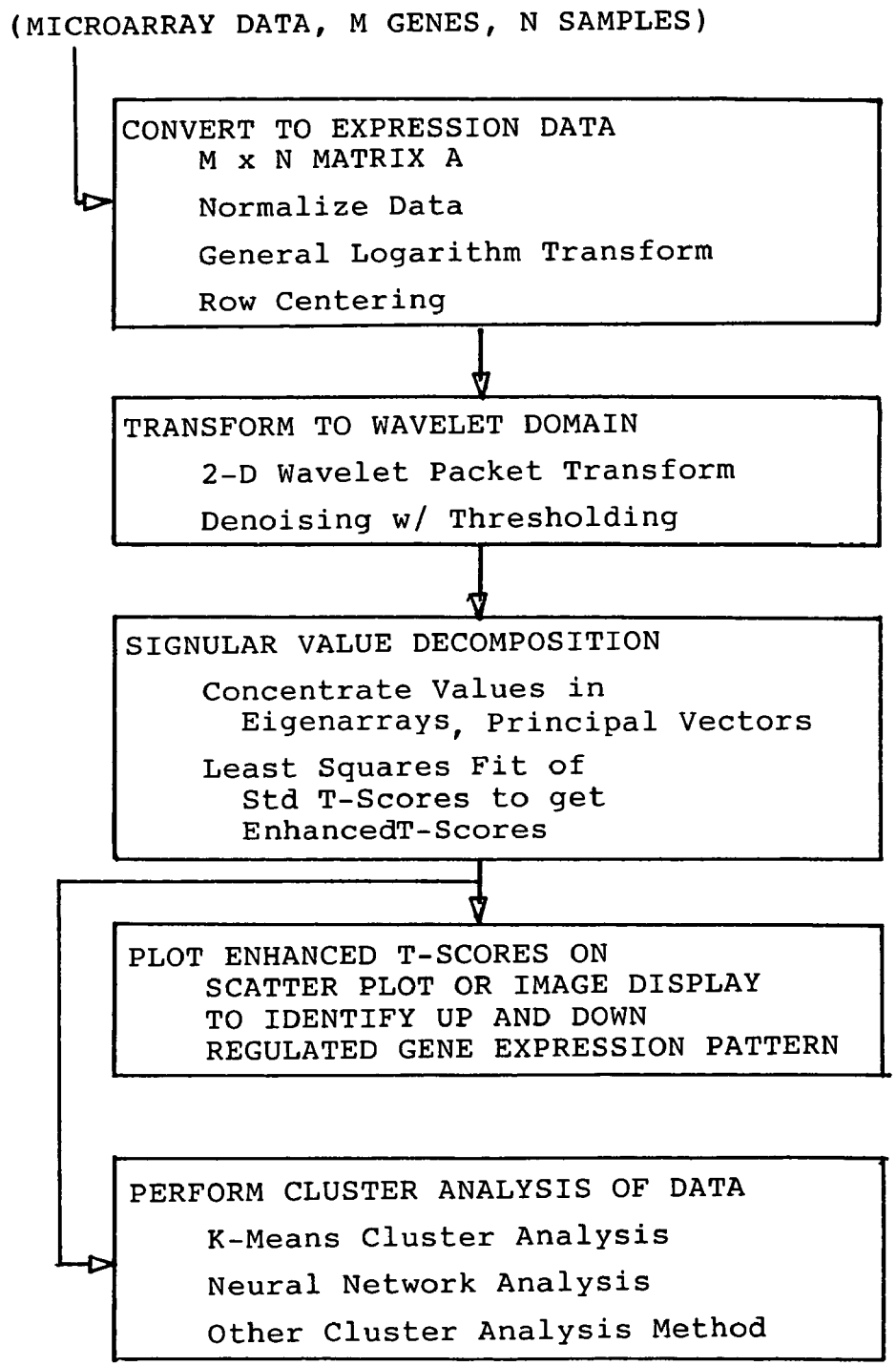
FIG. 1B is a flow diagram of an exemplary embodiment of the conversion of expression data to a scatter plot display to identify gene expression patterns.

As illustrated in FIG. 1A, the invention method first converts gene expression data from microarrays into a 2-D expression data matrix, analogous to 2-D image data. The transformation of gene chip data into an image data paradigm facilitates the use of powerful image data processing techniques. The conversion to an expression data matrix preferably includes data normalization, application of a general logarithm (glog) function to stabilize variation over intensity, and row-centering of the data matrix. As illustrated in FIG. 1B, the normalized, glogged and row-centered data matrix is then processed using a combination of 2D wavelet packet transform with denoising for increasing the signal-to-noise ratio of the expression data matrix, and singular value decomposition (SVD) of the expression data matrix for enhanced signal extraction. SVD captures the principal eigenarrays of the expression data matrix that represent the statistically significant differential gene expression patterns from the microarray data.

A step-by-step example of the application of the invention method is described in further detail below. In this example, raw simulated data for a limited set of genes in a small-sample study of cardiac risk patients were used for convenience in comparing the invention method to conventional gene data analysis techniques. However, it is understood that the invention method would be similarly applied to actual data from DNA microarray samples and could be used to test large gene sets or the whole human genome for sample populations of any size.

Expression Data Matrix

Referring again to FIG. 1A, $E=[e_{ij}]$ is an Expression Data Matrix of gene expression values for M rows of genes and N columns of gene probe samples. Each column $c_j$ consists of the entire array of M probe positions (indexed serially) on a microarray chip for a given sample. Each row $r_i$ consists of the gene expression values at a given gene probe position across all N samples. The gene expression values are the values obtained by measuring the intensity levels of the fluorescent tags reflecting the RNA transcripts in a nucleic acid sample that become hybridized to the probes of the microarray chip.

In this simulated data example, the Durbin-Rocke error model for gene expression was used to generate simulated probe values for 40 sample microarrays, each composed of 5000 genes. See Rocke, D. M., and Durbin, B., 2001, "A model for measurement error for gene expression arrays", J. Comp. Bio. 8, pp. 557-569. The 40 samples formed the columns of the expression data matrix where rows represented microarray gene probes and columns represented array samples. Columns 1-20 were labeled as control samples and columns 21-40 were labeled as treatment samples. Genes 1000-1099 were 2-fold up-regulated and genes 3000-3099 were 2-fold down-regulated, with all changes occurring in samples 21-25 only. Thus, 200 out of 5000 genes were changed in only 5 out of 20 treatment samples.

The gene expression values taken as raw data from microarray samples are initially normalized by standard data normalization techniques.

The raw data obtained from an unpaired experimental design are normalized using a the Robust Multichip Average (RMA) software package. See, Irizarry R. A., Bolstad B. M., Collin F., Cope L. M., Hobbs B. and Speed T. R. (2003), Summaries of Affymetrix GeneChip probe level data. *Nucleic Acids Research*, Vol. 31, No. 4, e15. RMA combines background correction, quantitation of gene expression and quantile normalization in a single processing algorithm. RMA quantitation estimates the log scale expression values using a robust linear fitting procedure known as median polish applied to perfect-match (PM) Affymetrix DNA probes only. The data are background corrected and quantile normalized prior to RMA quantitation. Note that RMA is essentially an additive model for the log2 transform of the background corrected and normalized PM fluorescence intensities.

For a paired-sample experimental design, we employ a lowess normalization procedure based on rank invariant genes. The unnormalized, background corrected RMA expression values for each gene are ordered for each chip of the paired sample. Genes whose ranking between the two chips is similar within a certain rank threshold are called invariant genes. A lowess curve fit is performed on the rank invariant genes only, resulting in a systematic error curve that reflects true systematic error without confounding with differential expression. This systematic error curve is used to rectify the RI scatter plot of the data pair. The resulting RI plot should be centered and symmetrically distributed about zero indicating an absence of any systematic error.

Microarray data have complicated error structure that is dependent on fluorescence intensity. That is, the error is lognormally distributed for high intensity values and normally distributed for low values. This dependence of intensity on mean expression level needs to be regularized prior to analysis using standard statistical methods. In general, log transformations provide good variance stabilization at high levels, but inflate the variance of observations that are below or near background. The glog transformation stabilizes the asymptotic variance of microarray data across the full range of the data and symmetrizes the underlying distribution. This allows further analysis to be performed on these data without violation of assumptions and without needing to remove low-level observations. See, Durbin B. P., Hardin D. M., Hawkins D. M. and Rocke D. M. (2002), A variance-stabilizing transformation for gene-expression microarray data, *Bioinformatics*, Vol. 18, Suppl. 1, pp. 105-110.

The expression data matrix is also row-centered. The mean expression profile is calculated by averaging the row profiles of the data matrix. The mean and profile is then subtracted from each row of the data matrix. The result is a transformed data matrix where each row is centered and hence comparable across all rows (i.e., genes) of the data matrix.

Wavelet Packet Transform

Conventional signal processing based on the Fourier transform utilizes analysis windows of fixed size, and is hence scale dependent. Only features that match the size of the analysis window are properly characterized. Signal features that are too small or too large with respect to the analysis window are either missed or inefficiently represented. Wavelet signal processing on the other hand analyzes a signal over a range of scales using analysis windows, or wavelets, of different time durations, thus providing a multiresolution signal analysis that is scale independent. The value of wavelet transform is that it captures both global and local features of the spectral signal. The wavelet transform acts like a signal processing microscope, zooming in to focus on small local features and then zooming out to focus on large global features. The result is a complete picture of all signal activity, large and small, global and local, low frequency and high frequency. A detailed description of a related continuous wavelet transform (CWT) as applied to image signal processing is described in PCT International Application US02/01585, entitled "Method and Apparatus for Generating Two-Dimensional Images of Cervical Tissue from Three-Dimensional Hyperspectral Cubes", filed in the name of inventors in common with the present application, and published as International Publication No. WO 02/057426 on Jul. 25, 2002, which is incorporated by reference herein.

In the wavelet domain, coherent signal components are localized at the larger scales of resolution while noise is confined to the smaller scales. Wavelet packets are an adaptive version of the standard wavelet transform. The wavelet packet transform generalizes the standard wavelet transform by decomposing both the approximation and detail signal simultaneously. See, Mallat, S., "A Wavelet Tour of Signal Processing", Academic Press, 1998. This separation of signal from noise allows the use of simple yet powerful denoising techniques based on the thresholding of wavelet coefficients. Coefficients with small absolute value are either set to zero or reduced and then what remains is inverted using the inverse wavelet packet transform to obtain a denoised version of the original signal. This denoised signal has a more uniform noise background, and enhanced signal and higher SNR. This simple procedure can be applied to 1-dimensional signals such as a gene expression profile for a single sample, or to 2-dimensional signals (image paradigm) for the expression data matrix of group samples.

In the present example, wavelet packet coefficients were thresholded using a single global parameter that applied to the entire data matrix. The normalized, row-centered expression data matrix was decomposed to level 3 based on the 2-dimensional wavelet packet transform based on the Haar mother wavelet and Shannon entropy criterion as implemented in the Matlab computational environment. Wavelet coefficients were selected on the best wavelet tree basis and the resulting histogram of wavelet coefficients was adaptively thresholded using a fixed form threshold equal to sqrt(2*log(N)) where N is equal to the total number of bins. The selected wavelet coefficients were then inverted back to the expression domain using the inverse wavelet packet transform to obtain the denoised data matrix.

Figure 2:
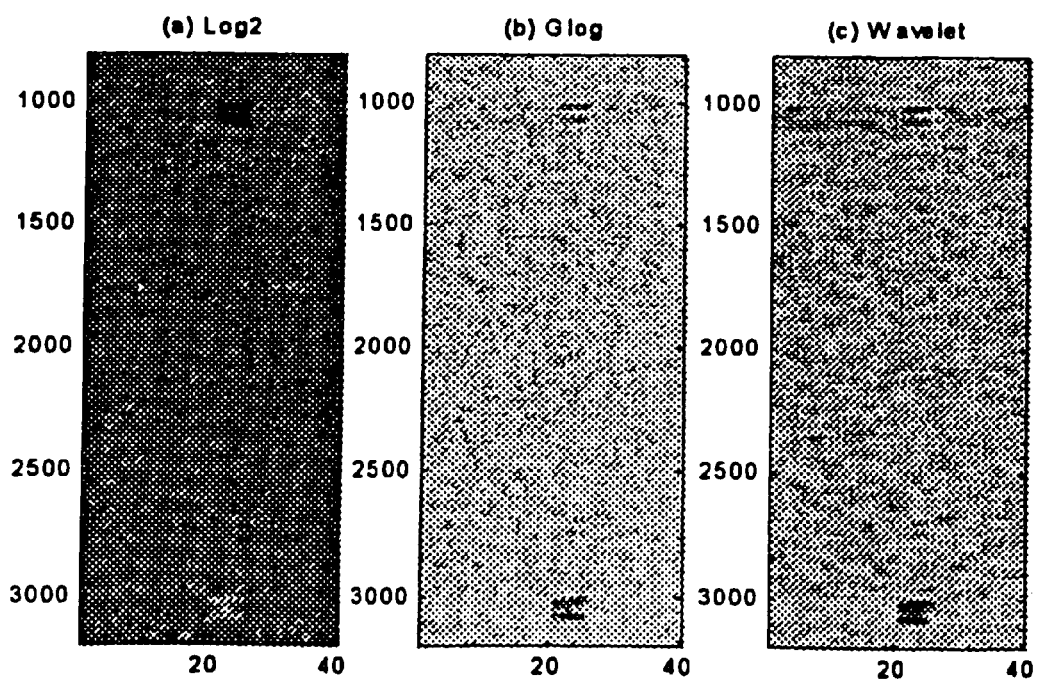
FIG. 2 shows a visual comparison of 2-D images of the gene expression data after (a) standard log2 processing; (b) glog transform; and (c) wavelet denoising of glogged data.

FIG. 2 shows a visual comparison of images of the gene expression data after (a) standard log2 processing, (b) glog transform, and (c) wavelet denoising of glogged data (according to the preferred approach in the present invention). The 2-D images were generated for genes 800-3200 (Y axis) and for samples 1-40 (X axis), with the gene expression values (probe intensity levels) shown as lightness-darkness levels. The simulated data were known to contain genes 1000-1099 that were 2-fold up-regulated and genes 3000-3099 that were 2-fold down-regulated, with all changes occurring in samples 21-25 only. Ideally, these areas should be visible as highly contrasting areas in the image. Note that almost no signal was visible in the log2 transformed data in image (a). The expression signal was more discernable in the glogged data of image (b) but the noise background was still quite active, which tended to degrade the signal and generate false positives. The wavelet denoised data in image (c) on the other hand shows a strong signal embedded in a uniform noise background, indicating a high signal-to-noise ratio (SNR). As shown further below, the wavelet-enhanced SNR translates to enhanced detection of differentially expressed genes for the simulated data set.

Combining SVD with Wavelet Processing

Previous methods have proposed enhancing the detection of genes that are differentially expressed between changed and unchanged samples based on singular value decomposition (SVD), for example, as described in: U.S. patent application 2002/019,704 of Tusher, V., Tibshirani, R., and Chu, C., published on Feb. 14, 2002; and also, Tibshirani, R. and Bair, E., "Improved detection of differential gene expression through the singular value decomposition", 2003, http://www-stat.stanford.edu/~tibs/; and Tusher, V., Tibshirani, R. and Chu, C., "Significance analysis of microarrays applied to transcriptional responses to ionizing radiation", Proceedings of the National Academy of Sciences, 98:5116-5121, 2001. In the present invention, s the results obtained are remarkably enhanced when wavelet denoising is applied to the data matrix in combination with applying SVD. This advantageous combination of wavelet denoising with SVD is referred to herein as "WSVD processing".

The advantages of WSVD processing were demonstrated for the present example using simulated microarray data generated by an implementation of the Durbin-Rocke error model for DNA microarrays. See, Rocke D. M and Durbin B. A (2001), A model for measurement error for gene expression arrays, *Journal of Computational Biology, Vol. 8, Number 6*). We generated a simulated data matrix A composed of 5000 rows and 40 columns where the rows represented genes and the columns samples. Note that the 40 samples were evenly divided between two biological conditions, which represented disease (columns 1-20) and control samples (columns 21-40). We also assume the data were properly normalized and glogged. In the simulation, we picked rows 1000-1099 to represent 100 genes that were expressed at a higher level in the disease versus control samples (up-regulation). We assigned to each gene an expression value that was 2-fold higher in the disease group than the control group. We also picked rows 3000-3099 to represent genes that were down-regulated between the disease and control group and assigned expression values that were 2-fold lower in the disease group than in the control group. RI scatter plots were used to confirm that the data were normalized and displayed the assumed noise structure. The goal was to see how many of the 200 up-regulated and down-regulated genes we could detect using the WSVD algorithm and compare the result with the standard t-test for detecting differentially expressed genes.

First, the simulated data matrix was wavelet denoised using the 2-dimensional Haar wavelet packet transform as describe above. Let A denote the wavelet denoised data matrix and e denote the 5000×1 column vector representing the standard t-scores for the rows of A assuming equal variance across biological conditions. We then take the SVD of A defined by $A=U*S*V^T$ where the columns of U and V are the eigenarrays and eigengenes of A, respectively and S is a diagonal matrix with entries representing the eigenexpression associated with each eigenarray-eigengene pair. Because SVD concentrates most of the signal information in the first k eigenarrays of U where k<<40 a representation of A in terms of these principal eigenarrays will have enhanced signal-to-noise ratio (SNR). A vector of enhanced t-scores, e*, was obtained by performing a least squares fit of the raw t-score vector e onto the principal eigenarrays of U using $e^*=\text{mean}(e)+\Sigma e^*u_k$. The enhanced t-score vector e* is thresholded to determine which genes are differentially expressed. Subsequent analysis shows that thresholding e* instead of e results in significantly improved detection of differentially expressed genes. Since SVD operates directly on A, computation of the sample covariance is unnecessary and the final result is more numerically stable than the standard statistical technique of finding the eigenstructure of $AA^T$.

Figure 3A:
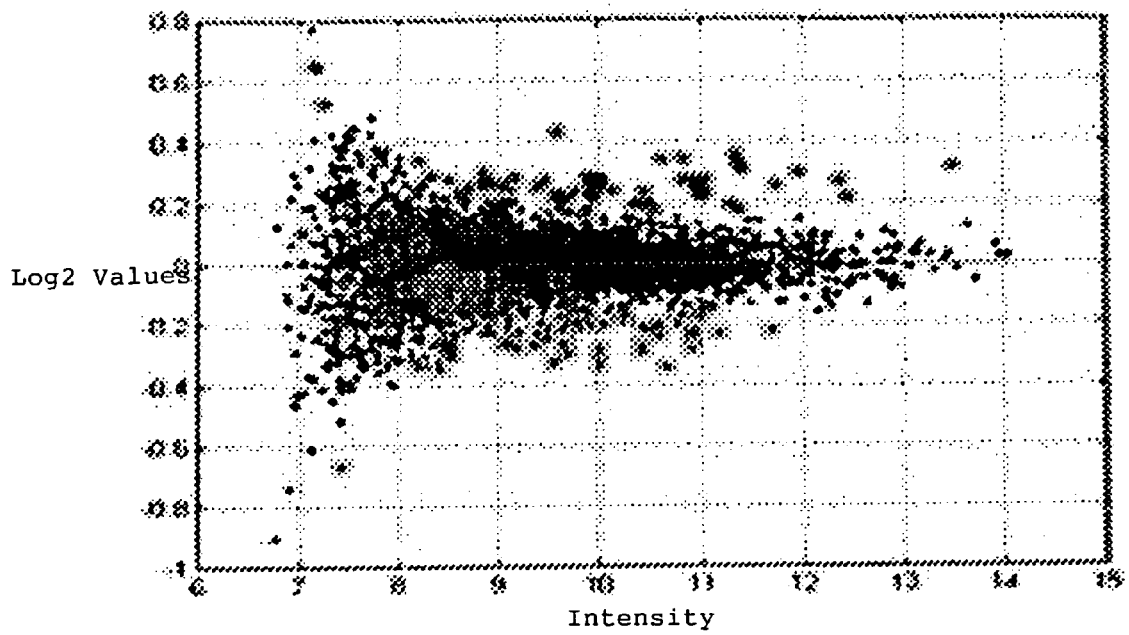
FIG. 3A is a standard scatter plot of geometric average of raw data (log2 scale) to intensity level showing how changed genes are buried in the background noise.

A comparison of the present method of wavelet packet denoising with SVD processing of the expression data matrix to conventional methods shows its capabilities to significantly enhance the detection of differentially expressed genes in microarrays. In FIG. 3A, a standard scatter plot is shown of the geometric average of raw data (log2 scale) to intensity level for the 40 simulated arrays. The lighter-contrast up-regulated genes (genes 1000-1099) appear above the zero axis and the down-regulated genes (genes 3000-3099) appear below the axis in contrast to unchanged or non-expressed genes and noise background (dark points). Note that many of the changed genes are buried in the background noise, making detection difficult. Also, no systematic errors were found to be present in the simulated data. When transformed using the generalized logarithm (glog) to stabilize variance over intensity, the glogged data were found to be more normally distributed than log2 transformed data, but still somewhat obscured in the background. As shown in FIG. 3B, the t-scores for the gene expression data were plotted after glogging but prior to WSVD processing. While the up-regulated genes 1000-1099 and down-regulated genes 3000-3099 can be discerned, the background noise was spread in a thick band that partially overlapped the differentially expressed genes. In contrast, the differentially expressed gene after full WSVD processing clearly stood out on the t-score chart, in FIG. 4, showing a marked separation of the changed genes from the thinned-down background noise.

Plotting the sum of the absolute values of the principal eigengene components over all samples and thresholding the resulting plot will identify samples that contribute most significantly to the detection differentially expressed genes. As a result, one can isolate both differential expression and the subset of chip samples that are most responsible for the observed effect. The samples that have lesser impact can then be removed from a subsequent analysis to improve detection performance.

A quantitative analysis based on computing a false discovery rate (FDR) was undertaken to analyze the confidence level that can be placed in the WSVD results. The effectiveness of WSVD processing was compared with SVD-only processing and glog-only (GLOG) processing using a true FDR (tFDR) computed for the known, simulated data. Here, tFDR is defined as the percentage of genes declared significantly changed that are actually false positives. Since the altered genes were chosen a priori for the data simulation, the number of false positives is known for any given threshold level. Hence, for simulated data, tFDR for either WSVD or the standard t-score is easily computed based on the ratio of the number of false positives to the total number of genes that break the threshold. In FIG. 5, tFDR was plotted against 11 points of possible ("called") significance ranging from 80 genes to 500 genes, comparing the results for WSVD, SVD-only, and GLOG-only processing. Note that the tFDR results from WSVD processing were uniformly lower for up to 500 significant genes when compared to SVD and GLOG processing. In particular, at 200 genes called significant (the number of genes known to be changed in the simulated data) on the horizontal axis of the tFDR plot, WSVD processing resulted in a reduction in tFDR by 92% with respect to GLOG-only processing and 77% with respect with respect to SVD-only processing. Monte Carlo simulations suggest that WSVD processing is consistently more powerful than the standard t-score based on a large number of simulations under a wide range of different scenarios.

In the case of using actual gene expression data from real trials, confidence level would be assessed by using an estimated FDR rate, since the actual number of false positives would not be known in advance. An estimated FDR (eFDR) rate can be computed by permuting the expression data. To determine FDR, we first take permutations of the denoised data matrix and recompute the WSVD scores for each gene based on the eigenstructure of the un-permuted data matrix, sorting the resulting vector for each such permutation. We define the expected distribution of WSVD scores as the median over all such vectors. A QQ-plot of the sorted observed scores versus the expected scores reveal genes that are significantly off the reference line, i.e., genes that are likely to be differentially expressed. We designate all genes with distance from the reference line greater than some positive threshold as significantly altered in expression. We assign an FDR value to this set of genes by finding all genes that are called significant for each permutation and take the average over all permutations. The ratio of this average number of false positives to the number of genes called significant is the estimated FDR for the gene list. We note that the use of FDR for assessing statistical confidence automatically accounts for the multiple testing of thousands of genes simultaneously for differential expression. Moreover, our use of permutation testing to estimate FDR obviates the need for any distributional assumptions regarding the data as is required in standard approaches to statistical hypothesis testing.

In the present example, the estimated FDR rate was computed based on computing 100 permutations for each significance call point. As shown in FIG. 6, the results from WSVD processing were uniformly better than either GLOG-only or SVD-only processing. Moreover, the computed eFDR for the simulated data appeared to be comparable to, and therefore a good approximation of, the tFDR rate. Since the tFDR would not be known for actual gene expression data taken in a real trial, this comparison indicates that the eFDR rate can be used as a reliable indicator of the comparative effectiveness of the WSVD method in real trials.

Moreover, a q-value is assigned to every gene, which measures the probability that the gene that is called significant is actually a false positive. The q-value for a specific gene is defined as the lowest FDR at which that gene is called significant. It corresponds to the well-known p-value, but is adapted to multiple testing situations. FDR and q-value are novel statistical measures of confidence that automatically take into account the huge mismatch between sample size and number of genes which is a common occurrence in DNA chip experiments.

Depending on the coherence and size of the sample population selected for a study, the differentially expressed genes may be more scattered or diffusedly distributed than in the above example using simulated data. Other analysis tools may also be employed to support the analysis of WSVD processed results for significant differentially expressed genes, such as various types of cluster analysis of significant groupings of differentially expressed genes.

Using WSVD when Small Sample Groups May Be Involved

A preferred approach to using the WSVD method employs a complementary pair of algorithms depending on whether a small number of samples in a group is involved. Genomic research using actual sample data is often conducted with a small number of subjects, due to the large data sets involved and the small sample population available that may fit highly specific disease-related parameters for the study. Two separate and distinct algorithms (as stated below) are used to optimally detect weak and/or inconsistent signals in DNA microarray data depending on the number of samples. A first algorithm employing the WaveThresh technique is used for a group of 1-5 samples or chips (a total of 10 samples overall, assuming two balanced groups). When there are more than 5 samples in a group, the sample number enables permutations of the data matrix to estimate the false discovery rate (FDR) for the gene list, so a second algorithm is used employing an "estimation-correlation" approach based on wavelet denoising and singular value decomposition, followed by thresholding to find an acceptable FDR. This leverages the number of samples to increase-SNR and enhance detection of differential expression. This approach may be applied to an unlimited number of samples. Although the WaveThresh technique can be used where more than 5 samples are involved, WaveThresh cannot be used to do an FDR estimate, which is a desirable quantitative measure of statistical significance.

Less than 5 samples in a group precludes an accurate estimate of FDR. Hence, a small group is defined from 1 to 5 samples. Since the small number of samples does not permit the use of estimating FDR, the WaveThresh technique locally applies to the RI scatter plot of WSVD-generated T-scores a universal threshold such as proposed by Donoho and Johnstone. See, Donoho D. L., Johnstone I. M., Kerkyacharian G. and Picard D. (1995), *Wavelet shrinkage: Asymptopia?, Journal of the Royal Statistical Society*, Ser. B, 57, pp. 301-369. The WaveThresh algorithm exploits the large number of genes by binning the RI data cloud by intensity. Indeed, variation in fold change as visualized in a typical RI scatter plot is co-varies with mean expression intensity such that variation increases as mean expression decreases. The binning process of the WaveThresh algorithm stabilizes variation within a bin so that the universal threshold can be applied to detect genes having similar fold change variation.

WSVD Algorithm for Sample Group N>5

When the number of samples is greater than five (5) samples in a group (10 total including a balanced number of controls), then the WSVD algorithm proceeds as previously described with the following more specifically defined steps:

(1) Vectorize appropriately normalized microarray data to form an M×N expression data matrix of M genes (rows) and N microarrays (columns) where the columns are grouped by biological condition (supervising vector);

(2) Apply a wavelet shrinkage technique based on a 1-dimensional wavelet packet transform to denoise each row of the expression data matrix to improve signal-to-noise ratio (SNR);

(3) Apply singular value decomposition (SVD) to the denoised data matrix to extract eigenarrays and eigengenes;

(4) Correlate eigengenes with a Haar step function (which takes on the value of +1 on treatment chip-samples and −1 on control chip-samples) and sort the resulting values in descending order;

(5) Pick the top K (K>0) eigengenes that correlate best with the Haar step function (principal eigengenes);

(6) Perform a least squares fit of the Haar step function on the principal eigengenes to obtain an empirical supervising vector to be used for correlation detection of differentially expressed genes;

(7) Correlate each un-denoised expression data for a gene with the denoised supervising vector described in step (6) to obtain a WSVD score for differential expression for each gene;

(8) Apply a threshold to the WSVD score for each gene to determine a set of differentially expressed genes;

(9) Estimate the false discovery rate (FDR) for the determined set of differentially expressed genes; and

(10) Modify the threshold for WSVD scores and repeat steps (8) and (9) until a significant set of differentially expressed genes with acceptable FDR is obtained.

The sequence of steps in the N>5 algorithm for WSVD processing is outlined in FIG. 7. In the Acquire Data step, the selected microarrays are hybridized to samples from each patient. For example, in one test of this algorithmic approach, whole-genome expression profiling is based on the new Affymetrix U133 Plus 2.0 GeneChip, which probes for over 47,000 human transcripts on a single microarray chip. This is in contrast to the U133A and B system which probes the human transcriptome using two (2) separate chips. The U133 Plus 2.0 chip is hybridized in solution to fluorescently labeled cRNA extracted from tissue samples.

In the Quantitate and Visualize steps, the expression level for each gene is quantified, normalized and log2 transformed using the Robust Multichip Average (RMA) software package. This pre-processing step accounts for probe-level measurement noise, systematic error and the inherent heteroscedasticity of microarray data with respect to level of expression. In the Normalize and Form Expression Data Matrix steps, Ratio-Intensity (RI) scatter plots that plot fold change versus average expression in log-log scale are used to visualize differential expression between paired samples or different response classes in order to assess data quality before and after normalization. After data pre-processing, a list of genes differentially regulated between two biological conditions, say, control and treated groups, is obtained using a novel algorithm that combines wavelet denoising and singular value decomposition (WSVDnew processing) together with an appropriate consideration of false discovery rates based on permutation testing.

In the Wavelet Denoise step, wavelet signal processing is used to denoise the rows of the normalized expression data matrix. Unlike averaging or other related noise reduction techniques that tend to blur sharp signal features, the multi-scale properties of the wavelet transform make it ideal for denoising gene expression profiles of differentially expressed genes which typically exhibit abrupt changes in magnitude at the boundaries of the response classes. In the SVD step, SVD is used to decompose the variation of the wavelet denoised data matrix into eigenarrays and eigengenes. We focus specifically on the eigengenes of the SVD analysis which provides an orthonormal basis within which expression profiles can be accurately approximated by a small subset of eigengenes. Then, the top K eigengenes that correlate best with the Haar step function are identified where the Haar step function is defined as taking on the value of +1 on the treated samples and −1 on the control samples. Next, the top K eigengenes are inverted back to the "sample" domain to obtain a new supervising vector that better reflects "true" differential expression over the sample chips.

Finally, in the Compute T-Scores steps, each gene is assigned a WSVD score for differential expression by correlating its un-denoised expression profile with the denoised supervising vector described above. We threshold the WSVD scores obtained for all 22,283 genes on the Affymetrix GeneChip to determine a list of genes differentially regulated-between multiple biological conditions. This thresholding procedure is based on the idea of false discovery rate (FDR) defined as the percentage of genes called significantly changed that are really false positives. To determine FDR, we first take permutations of the un-denoised data matrix and recompute the WSVD scores for each gene based on the eigenstructure of the un-permuted data matrix, sorting the resulting vector for each such permutation. We define the expected distribution of WSVD scores as the median over all such vectors. A QQ-plot of the sorted observed scores versus the expected scores reveals genes that are significantly removed from the reference line which indicates significant differential expression. We designate all genes with distance from the reference line greater than some positive threshold as significantly altered in expression. We assign an FDR value to this set of genes by finding all genes that are called significant for each permutation of the columns of the data matrix and take the average over all permutations. The ratio of this average number of false positives to the number of genes called significant is the estimated FDR for the gene list. We note that the use of FDR for assessing statistical confidence automatically accounts for the multiple testing of thousands of genes simultaneously for differential expression. Moreover, the use of permutation testing to estimate FDR obviates the need for any distributional assumptions regarding the data as is required in standard approaches to statistical hypothesis testing.

WSVD Algorithm for Sample Group N<6

In a small group where there are less than six (6) samples, the WSVD algorithm proceeds by an alternative algorithm with the following steps:

(1) Vectorize appropriately normalized microarray data to form an M×N expression data matrix of M rows (genes) and N columns (microarrays) where the columns are grouped as "treated" and "control" response classes in accordance with chip labels;

(2) Compute a single column vector, X, equal to the geometric mean of all sample chips in the treated response class;

(3) Compute a single column vector, Y, equal to the geometric mean of all sample chips in the control response class;

(4) Form an RI scatter plot having an R axis and an I axis where I=log2(X×Y) and R=log2(X/Y);

(5) Adaptively apply a binning technique to the I-axis of the RI scatter plot to ensure that each bin contains at least K genes per bin where K>75;

(6) Estimate the median absolute deviation (MAD) of expression values within each bin;

(7) Apply a threshold to each bin above and below zero using the value T=sqrt[2×(1−β)×log(K)]×MAD where:
  (a) $\beta=\log(\pi_0)/\log(\pi_1)$
  (b) log=natural logarithm
  (c) $\pi_0$=number of genes differentially expressed
  (d) $\pi_1$=total number of genes; and (8) Declare genes within a bin having a score greater than T as differentially expressed, as follows:
  (a) Call genes with score >T as differentially up-regulated
  (b) Call genes with score <−T as differentially down-regulated.

The sequence of steps in the N<6 algorithm for WSVD processing is outlined in FIG. 8. In the Acquire Data step, the selected microarrays are hybridized to fluorescently labeled cRNA extracted from tissue samples. The chips obtain data extracted from multiple "control" and "treated" tissue samples. In the Pre-Process Data and Form Expression Data Matrix steps, the expression level for each gene on the Affymetrix GeneChip is quantified, normalized and log2 transformed using the Robust Multichip Average (RMA) software package. This pre-processing step accounts for probe-level measurement noise, systematic error and the inherent heteroscedasticity of microarray data with respect to level of expression. In the Average Columns By Group step, the chips for each group are averaged in the log2 domain, or equivalently, geometrically averaged in the expression domain. This averaging process results in two "averaged" chips, one for each biological condition. Averaging also improves the signal-to-noise ratio (SNR) of the data. In the Visualize Data step, RI scatter plots are generated where the R-axis represents log2 of fold change and the variation of the data cloud varies with average intensity. A threshold is applied adaptively to the RI plot to generate a list of differentially expressed genes.

The WaveThresh binning (or banding) process uniformly bins the I-axis of the RI plot such that the bins overlap by 50%. The number of bins chosen in this initial step is user dependent where the default is set at 200 bins. The 200 uniformly spaced bins are then aggregated to form bins of varying lengths so that each resulting aggregated bin contains at least 75 genes. Anywhere from 90 to 100 aggregated bins of varying lengths that cover the I-axis is the final result. Each bin is then independently thresholded to detect differentially expressed genes. The results for each bin are then combined to arrive at an overall assessment of differential expression over the entire I-axis of the RI plot.

The unique features of applying the WaveThresh technique in this algorithm are as follows: (1) generation of a visually distinct RI plot to detect differential expression; (2) binning of the I-axis of the RI plot to stabilize intensity dependent variation of gene expression; (3) variable bin lengths ensuring enough data in each bin to ensure accurate estimation of variance for each bin; and (4) use of the fixed-form universal wavelet denoising threshold of Donoho and Johnstone for detecting differential expression in each bin independently (instead of the usual 2 or 3 sigma threshold used in classical statistics.)

In the Bin the RI Scatter Plot step, adaptive thresholding is achieved by binning the I-axis of the RI plot so that at least 90 bins are obtained, and each bin contains the expression values for at least 75 genes. The binning process described above essentially leverages the large number of genes to locally decouple variation from intensity within each bin. That is, we can assume that variation in each bin is more or less constant. We then compute positive and negative thresholds for each bin using $T=(\sqrt{2*(1-\beta)*\log(K)})*\sigma$ where $\beta$ is a function of number of genes that are truly changed, K is the number of genes in the bin and $\sigma$ is the standard deviation of gene expression within the bin. See, Sabatti C., Karsten S. and Geschwind D., *Thresholding rule for recovering a sparse signal from microarray experiments*, UCLA Statistics Technical Report #304.

In the Compute Threshold step, the threshold T is related to wavelet denoising where T is usually applied to the wavelet coefficients of a noisy signal. We have adapted the T-threshold to estimating the signal for differential expression as outlined by Sabatti C., et. al., hence, reference is made to use of the "WaveThresh" technique. Our adaptation of the T-threshold for the WaveThresh algorithm specifically involves locally thresholding the R values of the RI scatter plot based on adaptive binning of the intensity axis. In the Detect Differentially Expressed Genes step, all genes with absolute expression greater than T within a bin are declared differentially expressed. Genes with expression less than –T are down-regulated while up-regulated genes have expression greater than T. Doing this for each bin in succession results in an adaptive threshold that varies with gene intensity.

Figure 9:
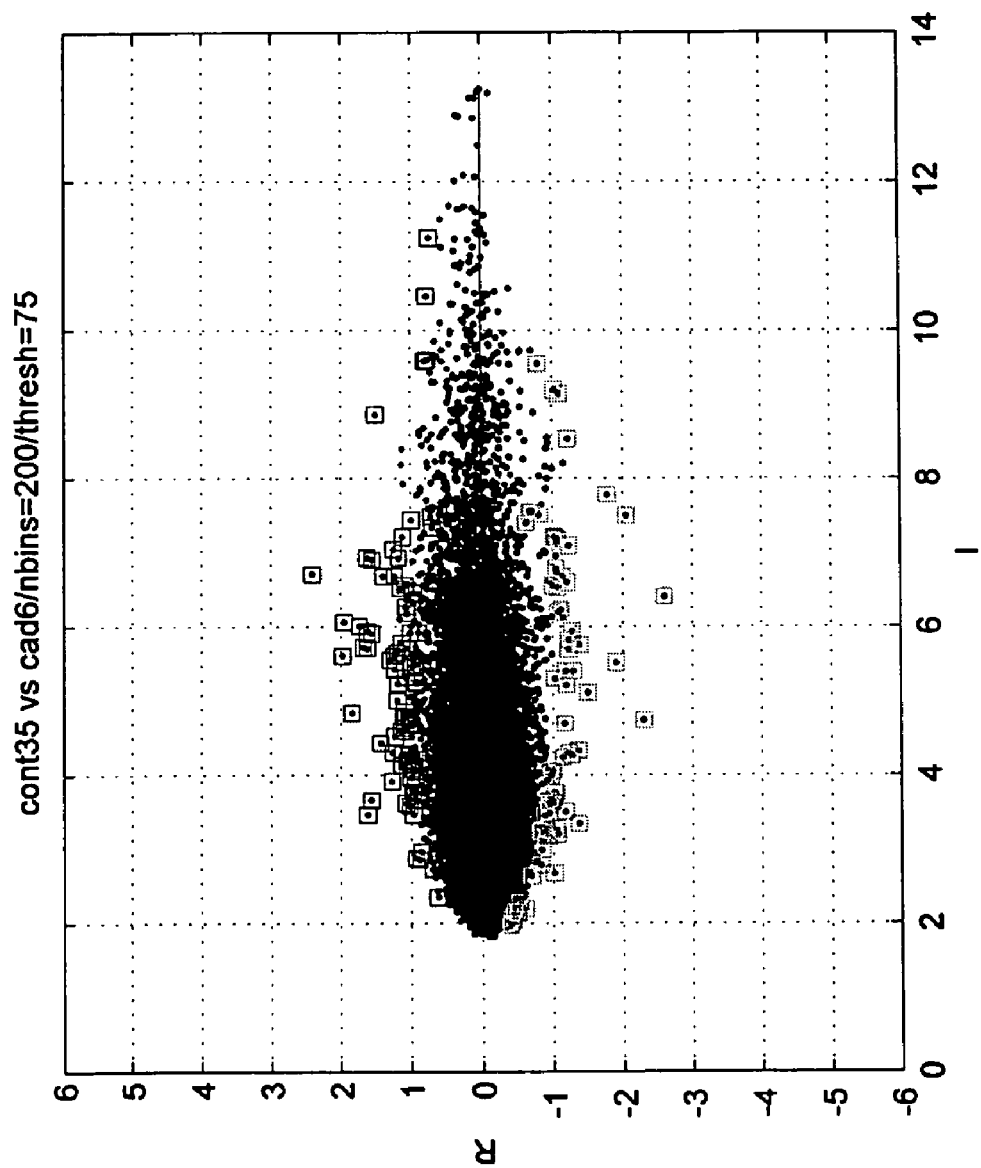
FIG. 9 shows differentially expressed genes obtained using the above-described process for N<6 samples with the WaveThresh algorithm.

FIG. 9 shows differentially expressed genes obtained using the above-described process for N<6 samples with the WaveThresh algorithm. This particular example compares Affymetrix U133A GeneChips hybridized to blood samples from two normal control patients and a single patient who experienced myocardial infarction (MI or heart attack) prior to age 50. Note we have only three chips in total (2 controls and 1 MI) to determine which genes out of 22,283 are different in terms of expression between the control group and the MI patient. The significant up-regulated genes are shown in red (above-axis squares) and significant down-regulated genes are shown in green (below-axis squares). Further bioinformatics analysis indicated that the resulting gene list was consistent with current literature on atherosclerosis and MI, thus, confirming the effectiveness of the algorithm for microarray experiments involving a small number of samples.

Figure 10:
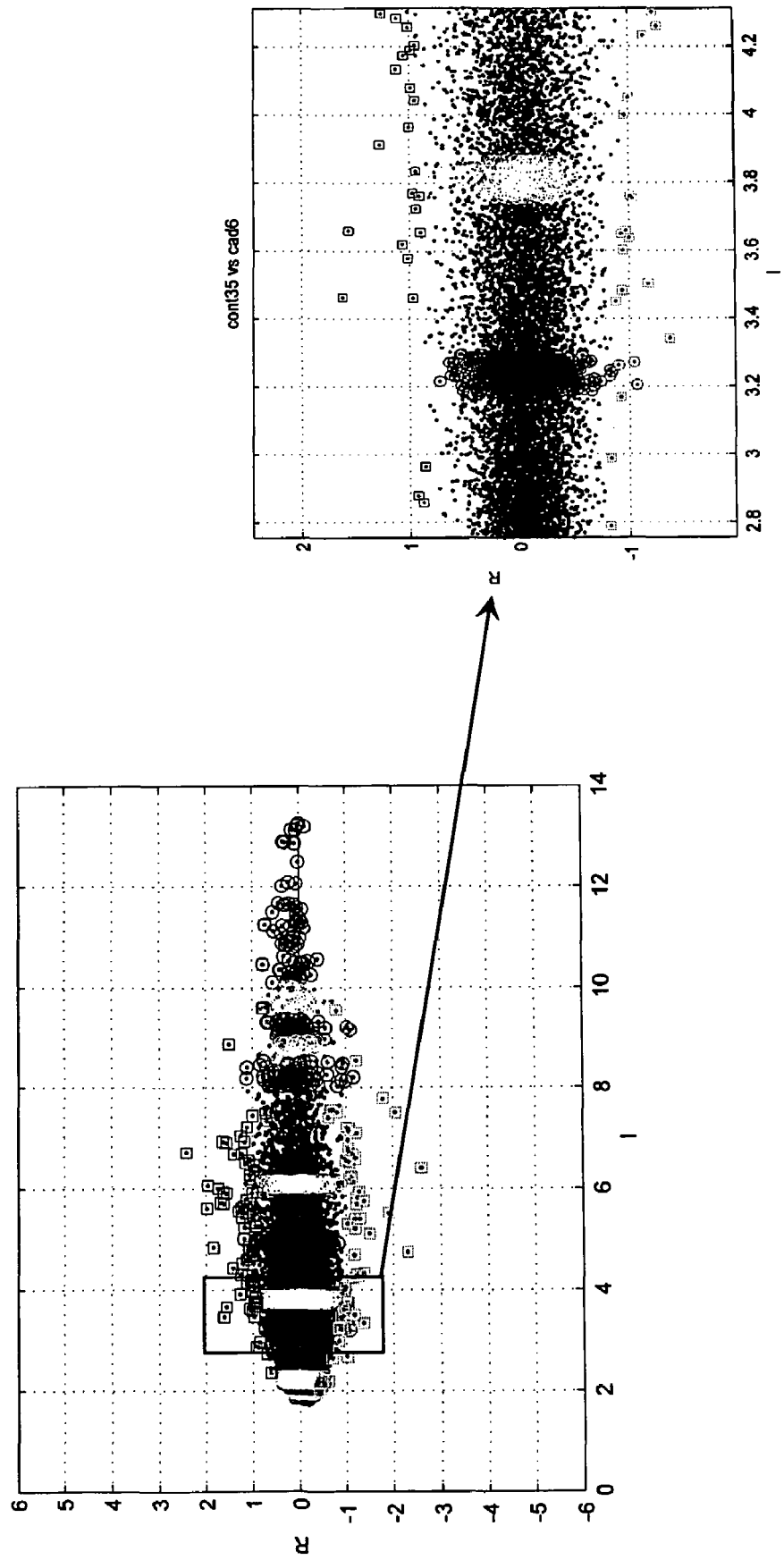
FIG. 10 illustrates the visual results on an RI scatter plot of the WaveThresh binning process for a microarray experiment.

FIG. 10 illustrates the visual results on an RI scatter plot of the WaveThresh binning process for the microarray experiment involving two normal controls and one MI patient. The black and yellow (dark/light) bands are examples of adaptive bins and the "points" they contain represent genes with almost constant variation and intensity. In actuality, the entire data cloud is tiled with black and yellow bins. Each bin has its own T threshold which is used to determine which genes within the bin are differentially expressed. The large black box focuses and zooms in (see figure on right) on two bins. Note that the black bin has several genes down-regulated, but no genes up-regulated. The down-regulated genes flagged in green appear to be separate and distinct from the main body of genes within the bin and are therefore likely to be differentially expressed. A similar analysis can be applied to the yellow bin.

In summary, the WSVD methods described herein can detect specific differential gene expression patterns in both small and large sample groups with an acceptable statistical confidence level. The data pre-processing steps disclosed herein are employed to improve the signal-to-noise ratio (SNR) of the expression data set such that the detection of differentially expressed genes is significantly enhanced. This approach broadens the analysis to one that characterizes both signal and noise, and employs algorithms better able to detect genes with weak differential expression due to small sample size and low SNR.

The enhanced capability to identify differentially expressed genes in any given study population makes WSVD an important tool for medical research. It would enable researchers to identify with high-confidence significant gene expression patterns in subject samples that would be suitable for studies in biomarker discovery, drug target validation, molecular diagnosis and prognosis, drug toxicity prediction and a systems-level understanding of disease biology, which can lead to the discovery of new diagnostic and prognostic applications and novel therapeutic interventions and drugs. The image charts resulting from WSVD processing, such as in FIG. 4, or the RI scatter plots in FIGS. 9 and 10, provide useful tools to enhance visual identification of differentially expressed gene patterns more distinctly from background noise.

The WSVD method may be extended to other fields of pattern analysis using large arrays of probe data. For example, as DNA microarrays measure the relative levels of mRNA transcribed by the protein-coding genes of the human genome, protein microarrays are expected to measure the relative levels of all proteins translated from every mRNA sequence of the human transcriptome. Protein microarrays are currently being developed that will interrogate the entire proteome just as DNA microarrays currently interrogate the entire transcriptome. Analysis of differential protein expression will likely require use of the same tools that have been developed for DNA microarray analysis. This is because protein expression patterns over thousands of proteins are indistinguishable from gene expression patterns over thousands of genes. Thus, the methods and tools described herein may become useful in even more powerful ways for correlation of protein expression patterns to biology and disease.

It is to be understood that many modifications and variations may be devised given the above description of the principles of the invention. It is intended that all such modifications and variations be considered as within the spirit and scope of this invention, as defined in the following claims.

The invention claimed is:

1. A method for enhanced detection and analysis of microarray samples each containing a large set of microarray gene probes, comprising the steps of:
    (a) transforming the microarray data into an M×N expression data matrix of M rows of microarray gene probes and N columns of microarray-detected gene expression values for the subject samples;
    (b) using a 2-dimensional wavelet transform to transform the expression data matrix into wavelet domain with denoising to enhance signal-to-noise ratio (SNR) of the expression data matrix;
    (c) applying a singular value decomposition (SVD) method to the wavelet-transformed and denoised expression data matrix in order to extract principal signals representing statistically significant differential gene expression patterns from the microarray data; and
    (d) generating an RI scatter plot from the SVD-applied expression data for visually identifying a gene expression pattern characteristic of a disease-related condition therefrom.

2. The method for enhanced detection and analysis of microarray data according to claim 1, wherein the microarray data are normalized for incorporation in the expression data matrix.

3. The method for enhanced detection and analysis of microarray data according to claim 1, wherein the microarray data are subjected to a generalized logarithm (glog) transformation to stabilize variance over intensity of expression values.

4. The method for enhanced detection and analysis of microarray data according to claim 1, wherein the microarray data are row-centered in the expression data matrix.

5. The method for enhanced detection and analysis of microarray data according to claim 1, wherein the wavelet transform is a 2-D wavelet packet transform of the Haar type.

6. The method for enhanced detection and analysis of microarray data according to claim 5, wherein denoising by wavelet packet transform is based on thresholding of wavelet coefficients, in which coefficients with small absolute value are either set to zero or reduced and then what remains is inverted using the inverse wavelet packet transform to obtain a denoised version of the original expression data matrix.

7. The method for enhanced detection and analysis of microarray data according to claim 6, wherein the wavelet packet coefficients were thresholded using a single global parameter that applied to the entire expression data matrix.

8. The method for enhanced detection and analysis of microarray data according to claim 7, wherein, for a wavelet-transformed-and-denoised expression data matrix A, the SVD method solves for $A=U*S*V^T$ where the columns of U and V are the eigenarrays and eigengenes of A, in order to concentrate most of the expression signal in the first k eigenarrays of U.

9. The method for enhanced detection and analysis of microarray data according to claim 8, wherein $k<<40$.

10. The method for enhanced detection and analysis of microarray data according to claim 8, wherein standard t-scores are computed for the expression data matrix and enhanced t-scores are obtained by performing a least squares fit of the standard t-scores onto the principal onto the principal eigenarrays of U.

11. The method for enhanced detection and analysis of microarray data according to claim 10, wherein permutation testing based on the enhanced t-scores is used to assign an estimated false discovery rate (eFDR) to a user-defined subset of genes deemed significantly changed based on the SVD-enhanced t-scores.

12. The method for enhanced detection and analysis of microarray data according to claim 10, wherein a t-scores chart is generated for visual display of the enhanced t-scores from combined wavelet denoising and SVD (WSVD) processing, for use as a visual tool to validate likely targets or groupings of differentially expressed genes.

13. The method for enhanced detection and analysis of microarray data according to claim 8, wherein the results of the combined wavelet denoising and SVD (WSVD) processing are used to generate a subset listing of significant differentially expressed genes based upon an acceptable estimated FDR rate.

14. A method for enhanced detection and analysis of microarray samples each containing a large set of microarray gene probes, depending on the number of samples in a group being analyzed, comprising:
    (A) If there are greater than (5) samples in the group, then the following steps of:
        (1) Vectorize appropriately normalized microarray data to form an M×N expression data matrix of M genes (rows) and N microarrays (columns) where the columns are grouped by biological condition (supervising vector);
        (2) Apply a wavelet shrinkage technique based on a 1-dimensional wavelet packet transform to denoise each row of the expression data matrix to improve signal-to-noise ratio (SNR);
        (3) Apply singular value decomposition (SVD) to the denoised data matrix to extract eigenarrays and eigengenes;
        (4) Correlate eigengenes with a Haar step function (which takes on the value of +1 on treatment chip-samples and −1 on control chip-samples) and sort the resulting values in descending order;
        (5) Pick the top K (K>0) eigengenes that correlate best with the Haar step function (principal eigengenes);
        (6) Perform a least squares fit of the Haar step function on the principal eigengenes to obtain an empirical supervising vector to be used for correlation detection of differentially expressed genes;
        (7) Correlate each un-denoised expression data for a gene with the denoised supervising vector described in step (6) to obtain a WSVD score for differential expression for each gene;
        (8) Apply a threshold to the WSVD score for each gene to determine a set of differentially expressed genes;
        (9) Estimate the false discovery rate (FDR) for the determined set of differentially expressed genes; and

(10) Modify the threshold for WSVD scores and repeat steps (8) and (9) until a significant set of differentially expressed genes with acceptable FDR is obtained; and (B) If there are less than six (6) samples in the group, then the following steps of:
  (1) Vectorize appropriately normalized microarray data to form an M×N expression data matrix of M rows (genes) and N columns (microarrays) where the columns are grouped as "treated" and "control" response classes in accordance with chip labels;
  (2) Compute a single column vector, X, equal to the geometric mean of all sample chips in the treated response class;
  (3) Compute a single column vector, Y, equal to the geometric mean of all sample chips in the control response class;
  (4) Form an RI scatter plot having an R axis and an I axis where $I=\log_2(X \times Y)$ and $R=\log_2(X/Y)$;
  (5) Adaptively apply a binning technique to the I-axis of the RI scatter plot to ensure that each bin contains at least K genes per bin where K<75;
  (6) Estimate the median absolute deviation (MAD) of expression values within each bin;
  (7) Apply a threshold to each bin above and below zero using the value $T=\sqrt{2 \times (1-\beta) \times \log(K)} \times MAD$ where:
    (a) $\beta = \log(\pi_0)/\log(\pi_1)$
    (b) log=natural logarithm
    (c) $\pi_0$=number of genes differentially expressed
    (d) $\pi_1$=total number of genes; and
  (8) Declare genes within a bin having a score greater than T as differentially expressed, as follows:
    (a) Call genes with score >T as differentially up-regulated
    (b) Call genes with score <−T as differentially down-regulated, and (C) Generate a visual display of the significant set of differentially expressed genes with acceptable FDR in step (A) or of the RI scatter plot from the threshold-applied expression data in step (B) for visually identifying a gene expression pattern characteristic of a disease-related condition therefrom.

15. The method adapted for identifying a disease-related condition in a sample population according to the method of claim 1.

16. The method adapted for diagnosing a disease state of an individual of a sample population according to the method of claim 1.

17. The method adapted for identifying a gene expression pattern characteristic of a disease-related condition in a sample population according to the method of claim 1.

18. The method adapted for developing a therapeutic or drug intervention for a disease-related condition by identifying a gene expression pattern characteristic of the disease-related condition in a sample population according to the method of claim 1.

19. The method adapted for generating a database of gene expression patterns characteristic of disease-related conditions according to the method of claim 1.

* * * * *